United States Patent [19]

Shimizu et al.

[11] Patent Number: 5,556,842
[45] Date of Patent: Sep. 17, 1996

[54] METHOD FOR VIABLE PRESERVATION OF LUNG GRAFTS

[75] Inventors: Nobuyoshi Shimizu; Kouzi Uno; Motoi Aoe, all of Okayama; Kenichi Yoshida, Ibaraki, all of Japan

[73] Assignee: Senju Pharmaceutical Co., Ltd., Osaka, Japan

[21] Appl. No.: 377,055

[22] Filed: Jan. 23, 1995

[30] Foreign Application Priority Data

Jan. 28, 1994 [JP] Japan ................... 6-008237

[51] Int. Cl.$^6$ ............... A61K 31/665; A61K 31/66; A61K 31/355; A61K 31/34
[52] U.S. Cl. ............ 514/100; 514/120; 514/129; 514/141; 514/146; 514/458; 514/474
[58] Field of Search ................... 514/100, 120, 514/129, 141, 146, 458, 474

[56] References Cited

U.S. PATENT DOCUMENTS

| 4,914,197 | 4/1990 | Yamamoto et al. ............ 536/117 |
| 5,306,713 | 4/1994 | Suetsugu et al. ............ 514/100 |

FOREIGN PATENT DOCUMENTS

| 0127471 | 12/1984 | European Pat. Off. |
| 0324387 | 7/1989 | European Pat. Off. |
| 0339486 | 11/1989 | European Pat. Off. |
| 0590514 | 4/1994 | European Pat. Off. |
| 2249937 | 5/1992 | United Kingdom. |

OTHER PUBLICATIONS

Tanemoto et al., Chemical Abstracts, vol. 119, No. 5, 2 Aug., 1993 Abstract 40876.
Senju Seiyaku, Database WPI, week 78829, Derwent Publications Ltd., London AN88–202095 JP-A-63 139 972 Jun., 1989.

*Primary Examiner*—Kevin E. Weddington
*Attorney, Agent, or Firm*—Wenderoth, Lind & Ponack

[57] ABSTRACT

This invention provides a lung graft preservative composition comprising a phosphoric acid diester compound of the formula:

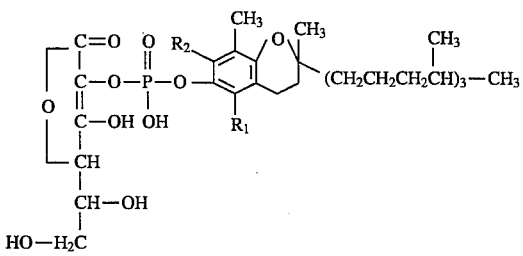

(wherein $R_1$ and $R_2$ are the same or different and each represents a hydrogen atom or a methyl group) or a pharmaceutically acceptable salt thereof and a method for the preservation of the lung graft using the compound.

2 Claims, 7 Drawing Sheets

5,556,842

METHOD FOR VIABLE PRESERVATION OF LUNG GRAFTS

BACKGROUND OF THE INVENTION

1. Field of the Invention

This invention relates to an improved lung graft preservative composition and an improved method for viable preservation of the lung graft for transplantation. More particularly, this invention relates to a lung graft preservative composition comprising an ascorbyl tocopheryl phosphate compound or a pharmacologically acceptable salt thereof and a method for viable preservation of a lung graft which comprises using said compound or salt.

2. Description of the Prior Art

For a successful organ transplantation, the organ resected from a donor must be kept functionally intact for a certain time period. Each kind of organ has its own characteristics and, hence, demands a unique protocol for viable storage. However, the preservation principles applicable to all organs in common are metabolic inhibition or metabolic maintenance.

For the viable preservation of the lung isolated For transplantation, (1) the donor core cooling method employing an extracorporeal circuit, (2) the method comprising flushing the pulmonary vascular bed with a perfusate from the pulmonary artery and, then preserving the lung under cooling, (3) the simple topical cooling method, and (4) the heart-lung autoperfusion method are known. Generally, however, for an effective cooling of the lung prior to resection, the method comprising flushing the lung from the pulmonary artery, immediately resecting the lung and immersing It in a preservative solution such as Euro-Collins solution is frequently employed.

However, it has been pointed out that these techniques have the drawback that on warm blood reperfusion of the lung after storage, pulmonary edema develops for some reasons or others so that the depression of the gas exchange function of the lung cannot be adequately prevented. Therefore, a more improved preservative for use in lung transplantation has been demanded and earnest research and development are in progress.

In the course of their ceaseless research into the pharmacology of ascorbyl tocopheryl phosphate compounds, the inventors of this invention discovered that these compounds are useful for the viable preservation of the lung isolated for transplantation. This discovery was followed by further studies which have resulted in the development of this invention.

SUMMARY OF THE INVENTION

This invention is, therefore, directed to: (1) A lung graft preservative composition comprising a phosphoric acid diester compound of the following formula or a pharmacologically acceptable salt thereof (hereinafter referred to briefly as the compound)

$$\begin{array}{c}\text{structure with } C=O,\ C-O-P-O-,\ C-OH,\ OH,\ CH,\ CH-OH,\ HO-H_2C,\ CH_3,\ R_2,\ O,\ CH_3,\ R_1,\ CH_3,\ (CH_2CH_2CH_2CH)_3-CH_3\end{array}$$

(wherein $R_1$ and $R_2$ are the same or different and each represents a hydrogen atom or a methyl group) and (2) a lung graft preserving protocol employing said composition.

Figure 1:
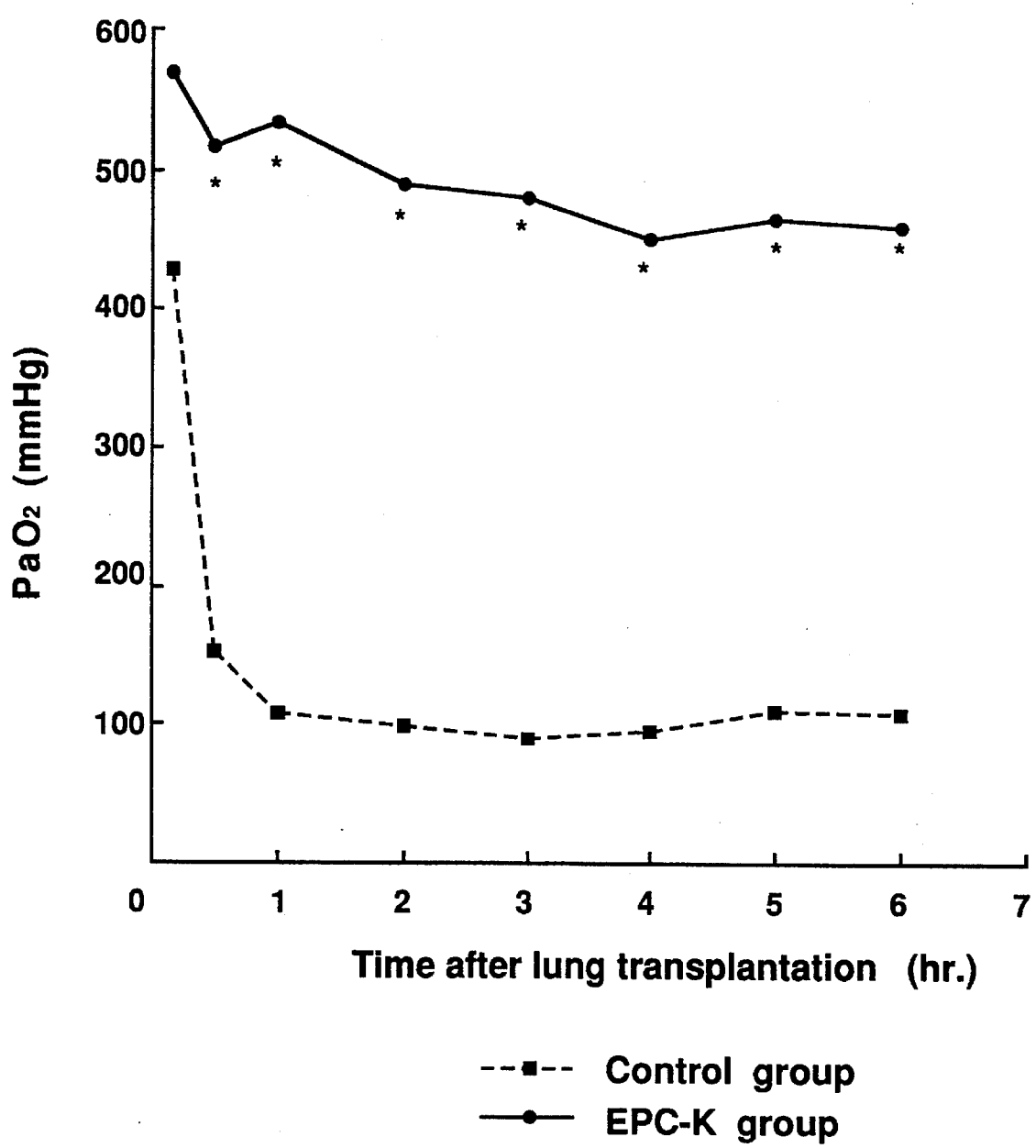
FIG. 1 represents arterial blood oxygen partial pressure after lung transplantation. The ordinate represents arterial blood oxygen partial pressure ($PaO_2$) (unit: mmHg) and the abscissa represents the time (unit: hr.) after lung transplantation.

The symbols used in FIGS. 1–7 represent:

● The group treated with the lung preservative composition of this invention

■ The group treated with Euro-Collins solution (control)

\* p<0.05

Each plot on the ordinate is a mean value.

DETAILED DESCRIPTION OF THE INVENTION

The compound for use in the lung graft preservative composition and lung graft preserving method of this invention can be synthesized by inter alia the process in Japanese Patent Publication H-2-44478 or Japanese Patent Application Kokai S-62-205091, or any improvement thereof.

The compound for use in the lung graft preservative composition and lung graft preserving method of this invention is already known to be useful as an anticataract agent, a prophylactic and therapeutic agent for crimacteric disturbance, a skin care cosmetic ingredient (Japanese Patent Publication H-2-44478), art antiinflammatory agent (Japanese Patent Publication H-1-27044), an antiulcer agent (Japanese Patent Application Kokai S-63-270626), and a prophylactic and therapeutic agent for ischemic organic impairment (Japanese Patent Application Kokai H-2-111722), among others. However, it is not known that this compound is useful for the preservation of the lung to be transplanted.

The compound for use in the lung graft preservative composition and lung graft preserving method of this invention may be whichever of its free form and in the form of a pharmacologically acceptable salt thereof and these substances can be selectively used according to the intended mode of use. The pharmacologically acceptable salt mentioned above includes, among others, salts with alkali metals such as sodium, potassium, etc. and salts with alkaline earth metals such as calcium, magnesium, etc. Other kinds of salts, if pharmacologically acceptable, can also be used likewise.

According to the clinical objective and need, more than one species of the compound can be incorporated, in an appropriate combination, in the lung graft preservative composition and preserving method of this invention.

The compound for use as the active ingredient in the lung graft preservative composition and preserving method of this; invention is a very safe substance with an extremely low toxic potential and, as such, can be used with advantage for the purposes of this invention. [e.g. the $LD_{50}$ values of L-ascorbyl DL-α-tocopheryl phosphate potassium (hereinafter referred to briefly as EPC-K)$\geq$5 g/kg p.o. (rats) and $\geq$100 mg/kg i.v. (rats)].

The lung graft preservative composition of this invention can be provided in a liquid form or supplied in a solid form for extemporaneous reconstitution. The solid form can be advantageously used as dissolved, suspended or emulsified in purified water, physiological saline or like medium. The solid form includes tablets, granules and powders, among others, which can be respectively manufactured by the known techniques. These preparations are preferably sterilized by known techniques such as membrane filtration or heat sterilization. Preparations may contain conventional additives such as an excipient, binder, buffer, isotonizing agent, stabilizer, pH control agent, preservative, solubilizer, thickening agent and so on.

Unless contrary to the object of this invention, the lung graft preservative composition of this invention may contain other organ-preserving ingredients which are generally used for the viable preservation of lung grafts. Among such ingredients are antibiotics, insulin, carbohydrates (mannitol, etc.), vitamins (vitamin C, vitamin E, etc.), organic acids (lactic acid, citric acid, etc.), nucleic acid bases (adenosine triphosphate etc.), antihypertensive agents (calcium-channel blockers, β-adrenergic antagonists, angiotensin-converting enzyme inhibitors, etc.), antiplatelet factor, antidiuretic hormone, anticoagulant (e.g. heparin) and so on.

Furthermore, the compound can be dissolved in the known organ preservative solution, such as Euro-Collins (EC) solution and University of Wisconsin solution [ViaSpan (registered trademark) produced by DuPont], to provide a lung graft preservative solution.

The lung graft preservative composition of this invention can be used in the known manner in which lung preservatives in general are employed in lung transplantation. For example, It can be used as follows. A sterilized cassette is filled with the lung graft preservative solution previously cooled to a predetermined temperature and the lung graft is placed in the preservative solution for cooling at a constant temperature. Then, a catheter is inserted into the pulmonary artery and the lung is perfused with the cooled preservative composition through the catheter to wash out the blood from within the organ. In the transplantation of a cadaver lung, the pulmonary vein is cut and the lung is perfused with the cooled preservative composition of this invention from the pulmonary artery, followed by resection of the lung. The thus-treated and resected lung is preserved at a constant low temperature in a sterile cassette filled with the preservative of this invention.

The proper concentration of the compound in the lung graft preservative composition of this invention is dependent on the species of compound, condition of the lung, and the necessary duration of preservation but the recommended final concentration in a liquid preparation is generally about $5 \times 10^{-9}$ g/ml to $5 \times 10^{-3}$ g/ml and preferably about $5 \times 10^{-8}$ g/ml to $5 \times 10^{-5}$ g/ml.

The osmolarity of such a liquid lung graft preservative composition of this invention is adjusted, by known means, to about 260 mOsm to about 360 mOsm, preferably about 275 mOsm to about 320 mOsm. The pH of the liquid preparation should also be adjusted, by known means, to about 3 to 10, preferably about 4 to 9.

The temperature suited for the lung graft preservation employing the preservative composition of this invention is dependent on the species and concentration of compound, condition of the lung and the desired duration of preservation but is generally about −5° C. to 20° and preferably about 0° C. to about 15° C.

In preserving the lung with the lung graft preservative composition of this invention, the known organ cassette, module and other hardware can be utilized.

EXAMPLES

The following test example and formulation examples are intended to illustrate this invention in further detail.

Example 1

Lung Preserving Effect of the Lung Graft Preservative Composition of this Invention in the Transplantation of Cardiac Arrest Donor Lungs The lung preserving effect of the lung graft preservative composition of this invention in the transplantation of cardiac arrest donor lungs was experimentally evaluated.

[Test substance] L-Ascorbyl DL-α-tocopheryl phosphate potassium (abbreviation: EPC-K) dissolved in modified Euro-Collins solution [1]

[Method] The left-lung transplantation model was constructed in adult mongrel dogs and used. The donor was brought to cardiac standstill by intravenous administration of potassium chloride solution and allowed to stand at room temperature for 2 hours. Then, while Group I (n=3) was perfused with Euro-Collins solution, an organ preservative which is commonly used in lung transplantation, Group II (n=3) was perfused with the lung graft preservative composition of this invention, followed by preservation at 4° C. for 12 hours. After the lung was transplanted into the recipient, the right pulmonary artery and right main branchus were ligated and the pulmonary function parameters were determined over a period of 6 hours. The results are shown in FIGS. 1–7.

Results

As shown in FIG. 1, the arterial blood oxygen partial pressure (PaO$_2$) was 108±38 mmHg in Group I vs. 460±94 mmHg in Group II after 6 hours. Results in Favor of Group II were obtained at other time-points, too.

Figure 2:
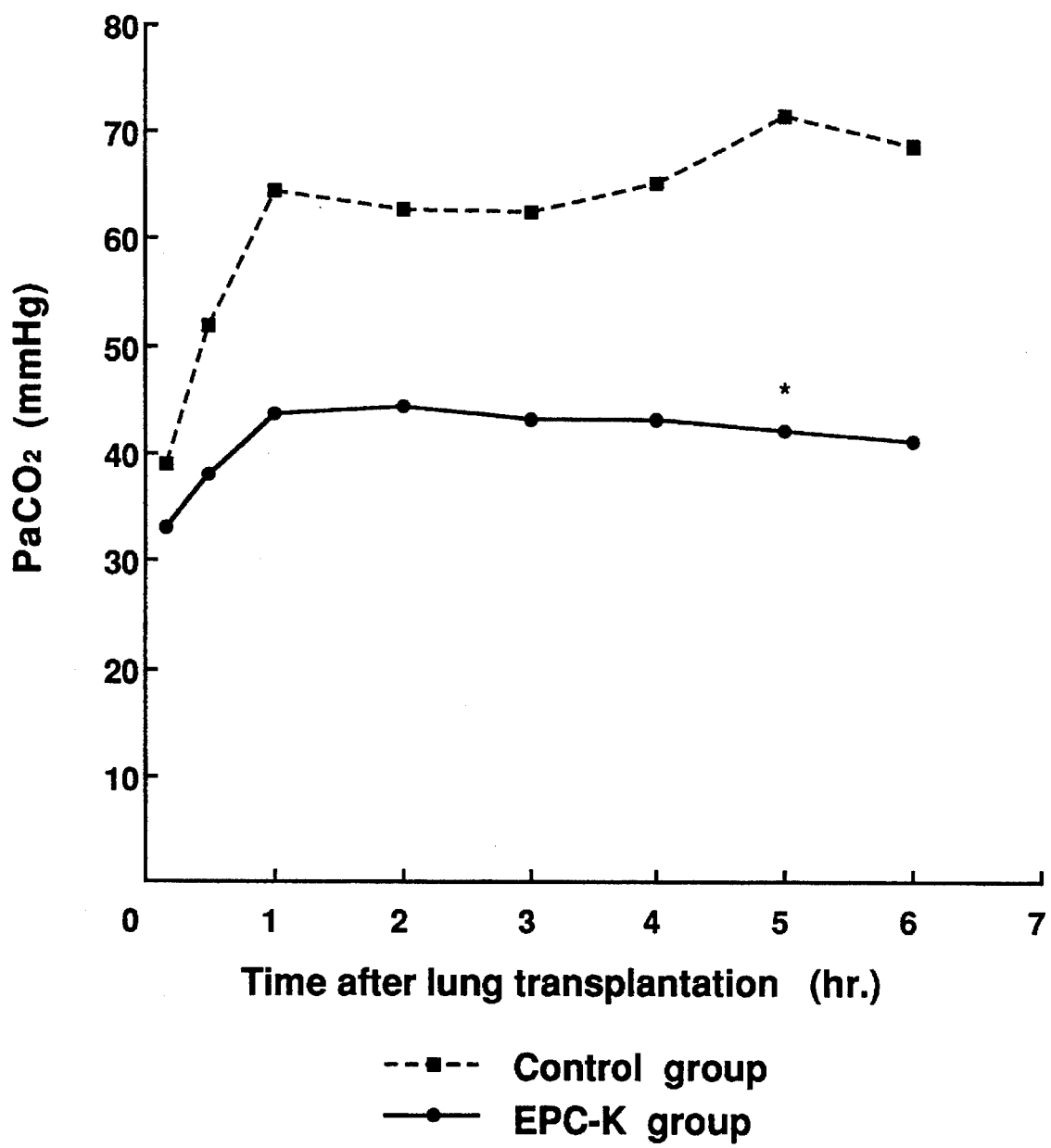
FIG. 2 represents arterial blood carbon dioxide partial pressure after lung transplantation. The ordinate represents arterial blood carbon dioxide partial pressure ($PaCO_2$) (unit: mmHg) and the abscissa represents the time (unit: hr.) after lung transplantation.

As shown in FIG. 2, the arterial blood carbon dioxide partial pressure (PaCO$_2$) after 5 hours was 71.4±11.2 mmHg in Group I vs. 32.4±20.9 mmHg in Group II, indicating that the lung graft preservative composition of this invention is remarkably effective.

Figure 3:
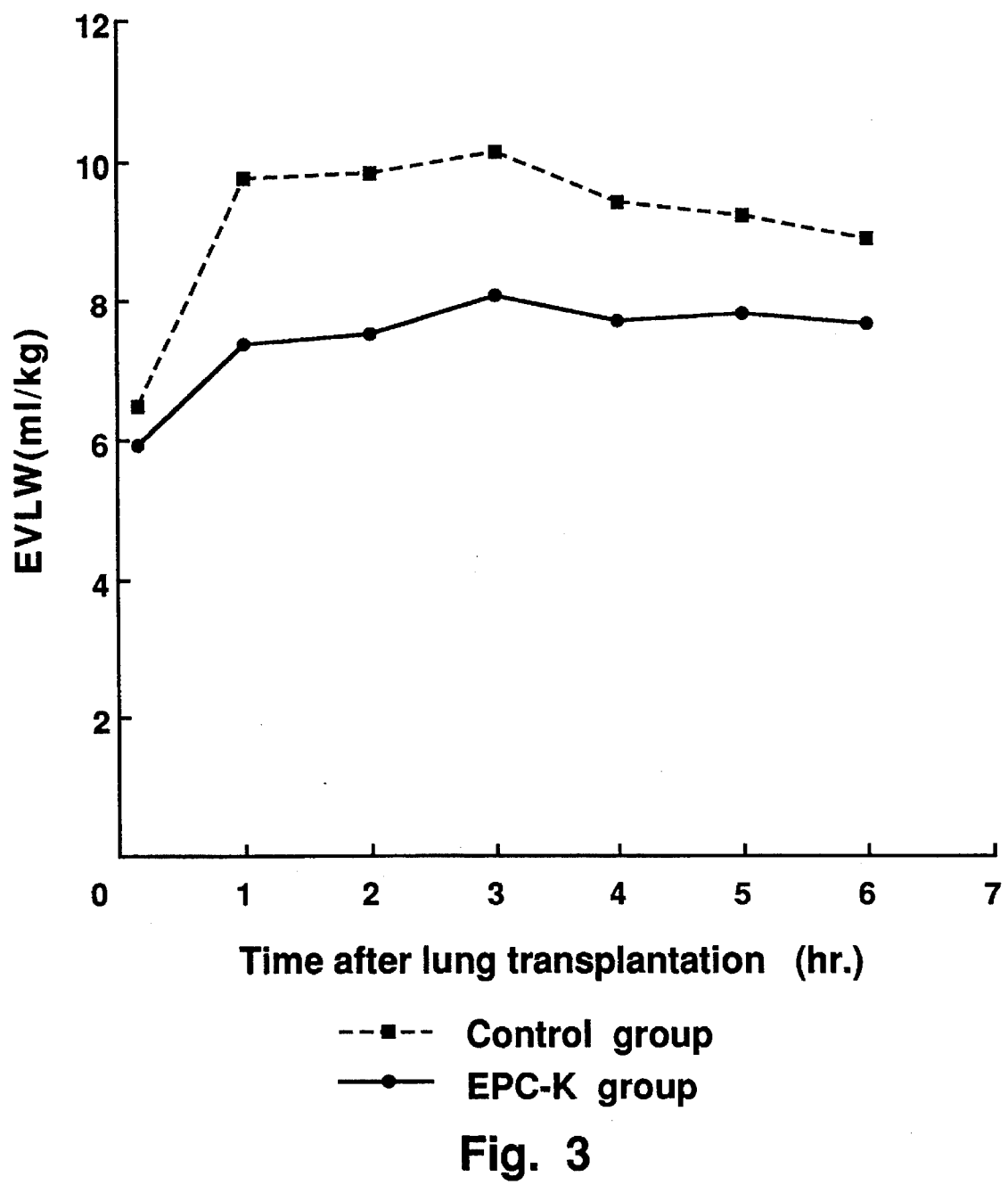
FIG. 3 represents extravascular lung water after lung transplantation. The ordinate represents extravascular lung water (EVLW) (unit: ml/kg) and the abscissa represents the time (unit: hr.) after lung transplantation.

As shown in FIG. 3, the value of extravascular lung water (EVLW) which is an indicator of pulmonary edema, indicates that the lung graft preservative composition of this invention is effective in inhibiting edema.

Figure 4:
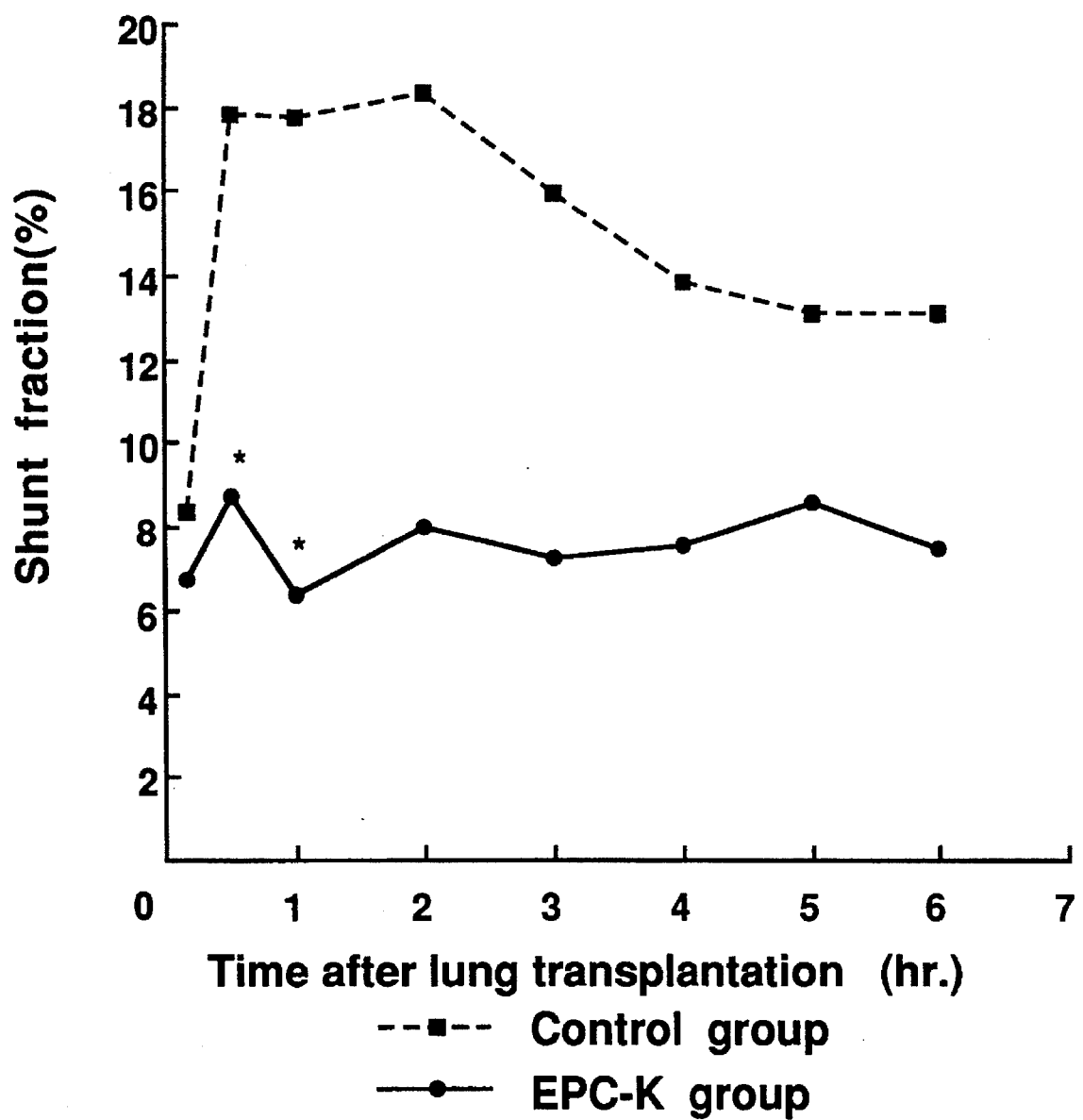
FIG. 4 represents blood shunt fraction after lung transplantation. The ordinate represents blood shunt fraction (unit: %) and the abscissa represents the time (unit: hr.) after lung transplantation.

The value of pulmonary blood shunt fraction, shown in FIG. 4, indicates that the lung graft preservative composition of this invention exerts a pulmonary blood shunt inhibitory effect which is significant after 1 and 2 hours. This inhibitory effect was also noted at other time-points.

Figure 5:
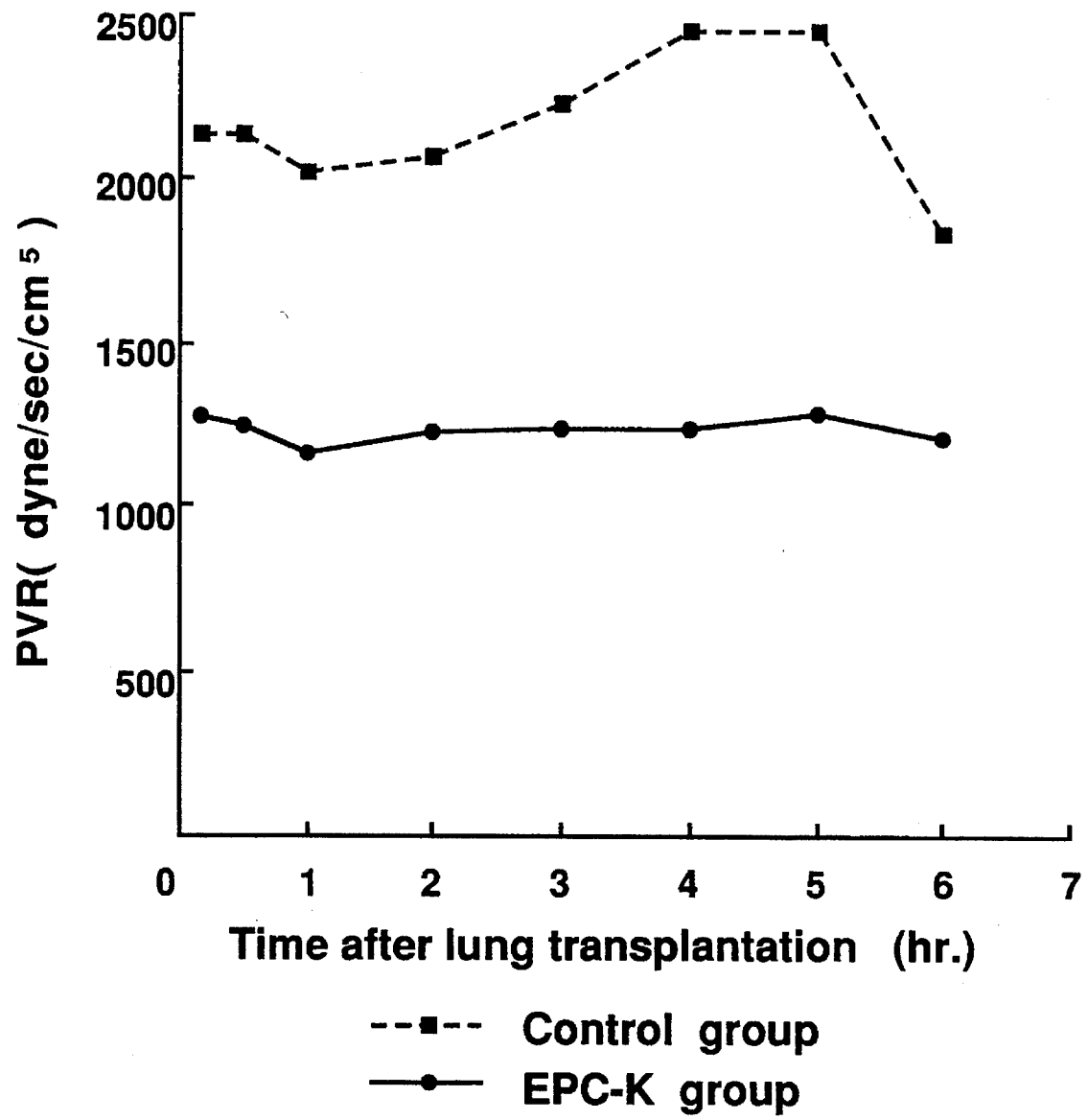
FIG. 5 represents pulmonary vascular resistance after lung transplantation. The ordinate represents pulmonary vascular resistance (PVR) (unit: dyne/sec/cm$^5$) and the abscissa represents the time (unit: hr.) after lung transplantation.

It is also apparent from the pulmonary vascular resistance (PVR) value given in FIG. 5 that the lung graft preservative composition of this invention inhibits the increase of pulmonary vascular resistance.

Figure 6:
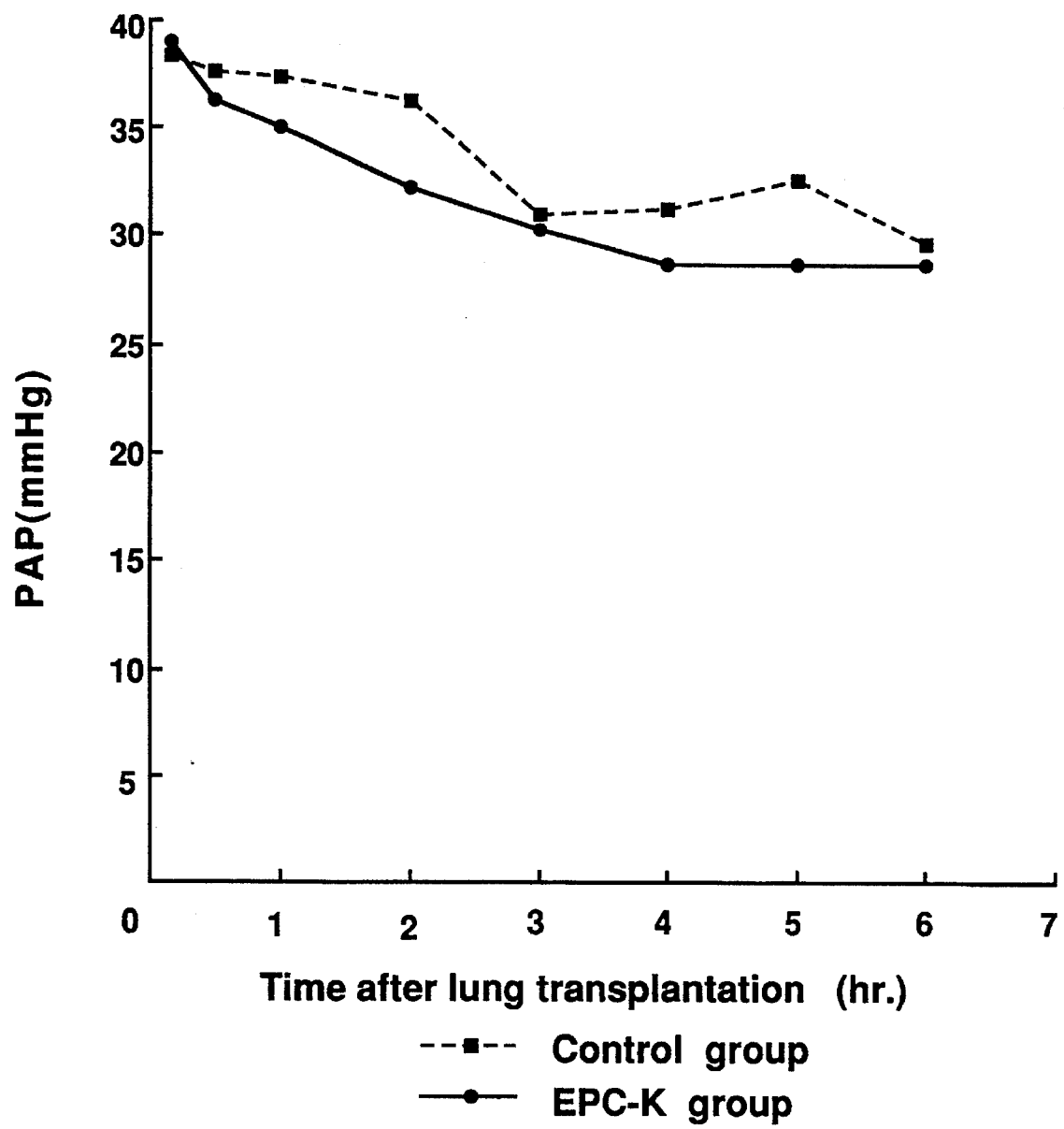
FIG. 6 represents pulmonary arterial pressure after lung transplantation. The ordinate represents pulmonary arterial pressure (PAP) (unit: mmHg) and the abscissa represents the time (unit: hr.) after lung transplantation.

The pulmonary arterial pressure (PAP) value shown in FIG. 6 indicates that the lung graft preservative composition of this invention inhibits pulmonary edema without increasing pulmonary vascular resistance.

Figure 7:
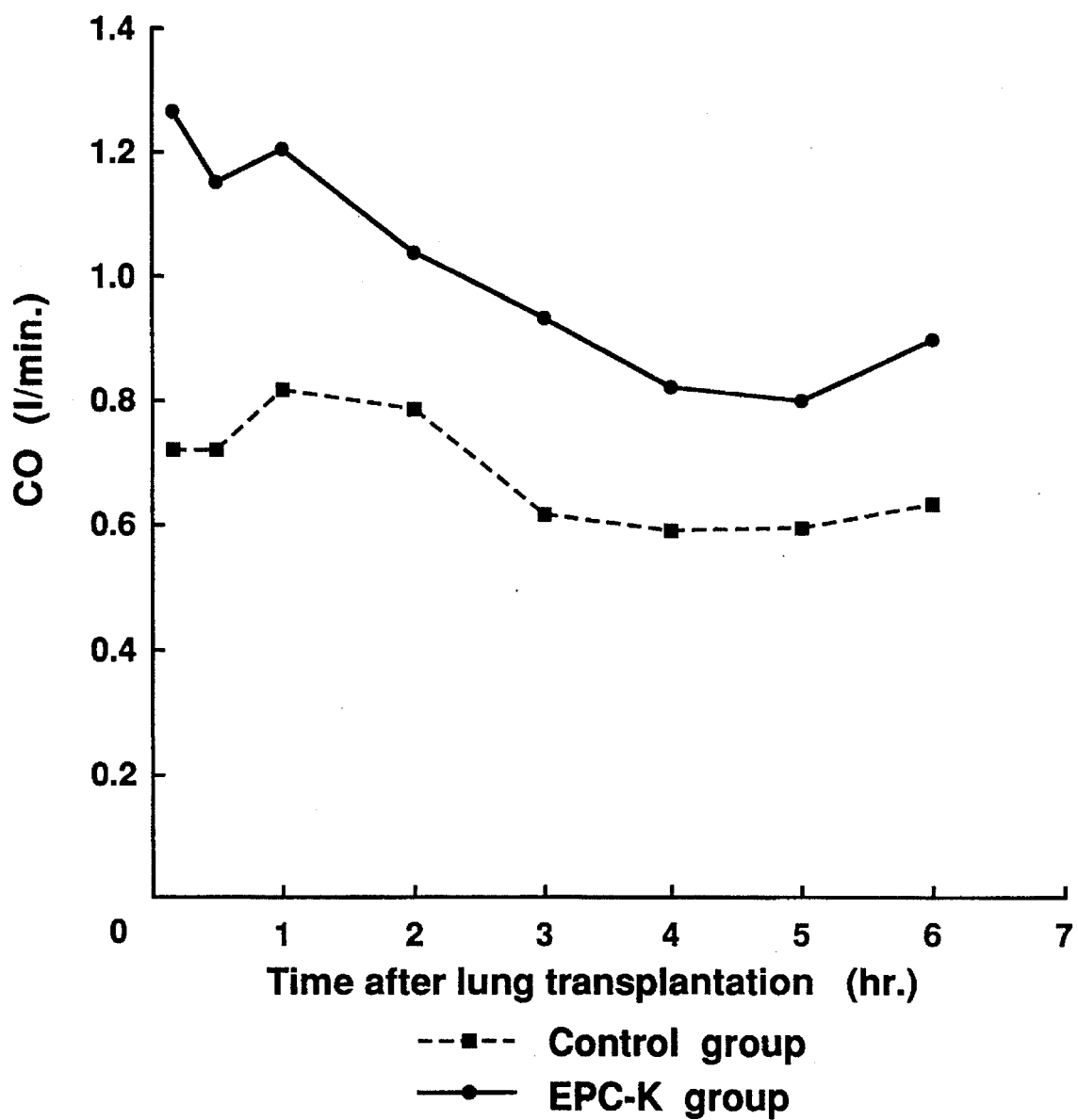
FIG. 7 represents cardiac output after lung transplantation. The ordinate represents cardiac output (CO) (unit: l/min.) and the abscissa represents the time (unit: hr.) after lung transplantation.

The cardiac output (CO) data shown in FIG. 7 indicates that the lung graft preservative composition of this invention exerts no adverse influence on the heart.

Thus, the lung graft preservative composition of this invention showed very favorable effects on various parameters of pulmonary function after blood reperfussion, suggesting that this preservative composition is useful for the viable preservation of cardiac arrest cadaver lungs.

| 1) Composition of Modified Euro-Collins Solution | |
|---|---|
| K$_2$HPO$_4$ | 7.40 g/l |
| NaHCO$_3$ | 0.84 g/l |
| KH$_2$PO$_4$ | 2.04 g/l |
| KCl | 1.12 g/l |
| MgSO$_4$ | 0.48 g/l |
| D50W | 50 ml/l |
| Heparin | 5,000 units/l |
| Osmolarity | 326 mOsm/kg |

Formulation Example 1

| | | |
|---|---|---|
| EPC-K | | 0.01 g |
| K$_2$HPO$_4$ | | 7.40 g |
| NaHCO$_3$ | | 0.84 g |
| KH$_2$PO$_4$ | | 2.04 g |
| KCl | | 0.6 g |
| MgSO$_4$ | | 0.48 g |
| Water for injection | | q.s. |
| Hydrochloride acid | | q.s. |
| Sodium hydroxide | | q.s. |
| | Total | 1000 ml |
| | pH | 7.3 |

The above ingredients are mixed in the conventional manner and sealed in a one-liter PVC bag to provide a lung graft preservative solution.

Formulation Example 2

| | | |
|---|---|---|
| EPC-K | | 0.1 g |
| Mannitol | | 5 g |
| Water for injection | | q.s. |
| Sodium hydroxide | | q.s. |
| | Total | 100 ml |
| | pH | 7.3 |

The above ingredients are mixed in the conventional manner and sealed in 2 ml glass ampules to provide an injectable solution.

This solution is extemporaneously mixed with an appropriate amount of an organ preservative, such as Euro-Collins or ViaSpan solution, to provide a lung preservative solution.

Example 3

| Solid preparation | |
|---|---|
| EPC-K | 10 mg |
| Sucrose | 500 mg |

The above solid preparation is dissolved in water for injection in the conventional manner and filled in 5 ml-glass vials to provide a lung graft preservative.

This preservative is extemporaneously mixed with an appropriate amount of an organ preservative solution, such as Euro-Collins or ViaSpan solution, to provide a lung graft preservative solution.

The lung graft preservative composition and preserving method of this invention produce excellent effects on various parameters of pulmonary function and can be used with advantage for the viable preservation of lung grafts.

What is claimed is:

1. A method for viable preservation of a lung graft which comprises immersing the lung graft after resection in a preservative solution containing a lung graft preserving effective amount of a phosphoric acid diester compound of the following formula or a pharmacologically acceptable salt thereof

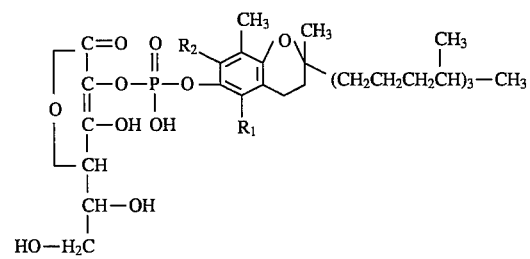

wherein R$_1$ and R$_2$ are the same or different and each represents a hydrogen atom or a methyl group.

2. The method as claimed in claim 1 wherein prior to resection the lung is flushed from the pulmonary artery with the preservative solution.

* * * * *